US009290581B2

(12) United States Patent
Poulter et al.

(10) Patent No.: US 9,290,581 B2
(45) Date of Patent: Mar. 22, 2016

(54) IMMOBILIZED PROTEINS AND METHODS AND USES THEREOF

(71) Applicants: Charles Dale Poulter, Park City, UT (US); Guillermo Roberto Labadi, Rasario (AR); Cecile Gauchet, Balma (FR); Rochelle Frances Hawkins Bohaty, Salt Lake City, UT (US)

(72) Inventors: Charles Dale Poulter, Park City, UT (US); Guillermo Roberto Labadi, Rasario (AR); Cecile Gauchet, Balma (FR); Rochelle Frances Hawkins Bohaty, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/139,440

(22) Filed: Dec. 23, 2013

(65) Prior Publication Data

US 2014/0378670 A1 Dec. 25, 2014

Related U.S. Application Data

(60) Division of application No. 13/482,512, filed on May 29, 2012, now abandoned, which is a continuation of application No. 12/225,359, filed as application No. PCT/US2007/007257 on Mar. 22, 2007, now Pat. No. 8,188,241.

(60) Provisional application No. 60/785,249, filed on Mar. 22, 2006.

(51) Int. Cl.
| | |
|---|---|
| *C07K 17/14* | (2006.01) |
| *C07K 1/107* | (2006.01) |
| *C07K 1/113* | (2006.01) |
| *C07K 14/435* | (2006.01) |
| *C12N 9/10* | (2006.01) |
| *G01N 33/543* | (2006.01) |
| *G01N 33/552* | (2006.01) |
| *C07K 14/00* | (2006.01) |
| *C12P 21/00* | (2006.01) |

(52) U.S. Cl.
CPC ............. *C07K 17/14* (2013.01); *C07K 1/1077* (2013.01); *C07K 1/1133* (2013.01); *C07K 14/00* (2013.01); *C07K 14/43595* (2013.01); *C12N 9/1088* (2013.01); *C12P 21/00* (2013.01); *G01N 33/54393* (2013.01); *G01N 33/552* (2013.01)

(58) Field of Classification Search
None
See application file for complete search history.

(56) References Cited

U.S. PATENT DOCUMENTS

2005/0048192 A1  3/2005 Raines et al.
2005/0106627 A1* 5/2005 Zhao et al. ............... 435/7.1

OTHER PUBLICATIONS

Kho et al., "A tagging-via-substrate technology for detection and proteomic of farnesylated proteins", PNAS, 2004, 101(34):12479-84.*
Rose et al. Enzymatic incorporation of orthogonally reactive prenylazide groups into peptides using geranylazide diphosphate via protein farnesyltransferase: Implications for selective protein labeling:, Biopolymers (Pept Sci) Apr. 2005.*
Rose et al., "Evaluation of geranylaizde and farnesylazide diphosphate for incorporation of prenylazides into a CAAX box-containing peptide using protein farnesyltranferase", J. Peptide Research, 2005, 65:529-537.*
Breinbauer et al.; "Azide-Alkyne Coupling: A Powerful Reaction for Bioconjugate Chemistry"; ChemBioChem—A European Journal of Chemical Biology, vol. 4, No. 11; Nov. 2003; pp. 1147-1149.
Franke et al.; "Peptide ligation through click chemistry for the generation of assembled and scaffolded peptides"; Tetrahedron Letters 46, Apr. 2005; pp. 4479-4482; Elsevier Ltd.
Gauchet et al.; "Regio-and chemoselective Covalent Immobilization of Proteins through Unnatural Amino Acids"; J. Am. Chem. Soc. 2006, 128, pp. 9274-9275.
Harris et al.; "Modulation of the Zinc (II) Center in Protein Farnesyltransferase by Mutagenesis of the Zinc (II) Ligands"; Biochemistry 2002, 41, pp. 10554-10562. American Chemical Society.
Hartman et al.; "Peptide Specificity of Protein Prenyltransferases is Determined Mainly by Reactivity Rather than Binding Affinity"; Biochemistry 2005, 44; pp. 15314-15324. American Chemical Society.
Kho et al.; "A tagging-via-substrate technology for detection and proteomic of farnesylated proteins;" PNAS; Aug. 24, 2004, vol. 101, No. 34, pp. 12479-12484.
Parrish et al.; "PEG- and Peptide-Grafted Aliphatic Polyesters by Click Chemistry"; J. Am. Chem. Soc. vol. 127, No. 20; Jan. 2005; pp. 7404-7410. American Chemical Society.
PCT Application No. PCT/US07/07257; Filing date Mar. 22, 2007; University of Utah Research Foundation; International Search Report mailed Sep. 17, 2008.
Rose et al.; "Enzymatic Incorporation of Orthogonally Reactive Prenylazide Groups into Peptides Using Geranylazide Diphosphate Via Protein Farnesyltransferase: Implications for Selective Protein Labeling"; Biopolymers, 2005, vol. 80, No. 2-3; pp. 164-171.
Rose et al.; "Evaluation of geranylazide and farnesylazide disphosphate for incorporation of prenylazides into a CAAX box-containing peptide using, protein farnesyltransferase"; J. Peptide Res., 65, 2005; pp. 529-537; Blackwell Munksgaard 2005.

(Continued)

*Primary Examiner* — Suzanne M Noakes
(74) *Attorney, Agent, or Firm* — Thorpe North & Western, LLP

(57) ABSTRACT

The invention relates to the field of covalently attaching proteins to a substrate, particularly to methods of immobilizing proteins by posttranslationally modifying a cysteine residue of said protein through the addition of functional groups. The invention also relates to biological molecules used in such techniques, including proteins, and detection methods and kits that utilize such immobilized proteins, such as a microdevice or "protein chip", a high-throughput screening device, and for the microscopy of proteins on a surface.

13 Claims, 13 Drawing Sheets

(56) References Cited

OTHER PUBLICATIONS

Soeliner et al.; "Site-Specific Protein Immobilization by Staudinger Ligation"; J.Am. Chem. Soc., 2003; 125; pp. 11790-11791.

Sun et al.; "Carbohydrate and protein immobilization onto solid surfaces by sequential Diels-Alder and azide-alkyne cycloadditions"; Bioconjugate Chemistry, Jan. 2006, vol. 17, No. 1; pp. 52-57; American Chemical Society.

U.S. Appl. No. 12/225,359, filed Sep. 18, 2008; Charles Dale Poulter; Office Action dated Sep. 10, 2010.

U.S. Appl. No. 12/225,359, filed Sep. 18, 2008; Charles Dale Poulter; Office Action dated Feb. 15, 2011.

U.S. Appl. No. 12/225,359, filed Sep. 18, 2008; Charles Dale Poulter; Notice of Allowance dated Feb. 3, 2012.

U.S. Appl. No. 13/482,512, filed May 29, 2012; Charles Dale Poulter; Office Action dated Jul. 2, 2013.

Zhou et al.; "A Fluorogenic Probe for the Copper(I)-Catalyzed Azide—Alkyne Ligation Reaction: Modulation of the Fluorescence Emission via $^3(n,\pi^*)$-$^1(\pi,\pi)$ Inversion"; J. Am. Chem. Soc., vol. 126, No. 29; 2004; pp. 8862-8863; American Chemical Society.

\* cited by examiner

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
ccggtagcat gcatgagtaa aggagaag                                      28

<210> SEQ ID NO 2
<211> LENGTH: 57
<212> TYPE: DNA
<213> ORGANISM: Artificial Sequence
<220> FEATURE:
<223> OTHER INFORMATION: Primer

<400> SEQUENCE: 2
gacgataagc ttttaagcaa taacgcacct agttcgtttg tagagctcat ccatgcc      57

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
atacataagc ttatgtcccc tatactaggt tat                                33

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4
tgaaccaagc ttttaggcta taacacagcg cgtacgatcc gattttggag g            51
```

IMMOBILIZED PROTEINS AND METHODS AND USES THEREOF

PRIORITY DATA

This application is a continuation of U.S. patent application Ser. No. 13/482,512, filed May 29, 2012, which is a continuation of U.S. patent application Ser. No. 12/225,359 filed on Sep. 18, 2008, now issued as U.S. Pat. No. 8,188,241, which is the national phase filing under 35 U.S.C. 371 of PCT Application No. PCT/US2007/007257, filed Mar. 22, 2007, which claims the benefit of U.S. Provisional Patent Application Ser. No. 60/785,249, filed Mar. 22, 2006, each of which are incorporated herein by reference.

GOVERNMENT INTEREST

This invention was made with government support under GM021328 awarded by the National Institutes of Health. The government has certain rights in the invention.

FIELD OF THE INVENTION

The present invention relates to the field of covalently immobilizing proteins on a substrate, particularly to methods of immobilizing proteins by posttranslationally modifying a cysteine residue of said protein through the addition of functional groups.

The present invention also relates to biological molecules used in such techniques, including proteins, and detection methods and kits that utilize such immobilized proteins, such as a microdevice or "protein chip", a high-throughput screening device, and for the microscopy of proteins on a surface.

BACKGROUND OF THE INVENTION

Proteins are immobilized to various surfaces for a myriad of purposes, such as in the production of protein "chips" or other analytical tools useful in studying protein-ligand and protein-protein interactions. Devices in which such proteins are immobilized covalently are generally more robust than their non-covalent counterparts.

Typically covalent immobilization has been accomplished through reactions between electrophilic reagents and exposed nucleophilic hydroxyl, amino, carboxylate, and sulfhydryl moieties found in the side chains of naturally occurring amino acids located on the surface of proteins. This approach has two problems. It is difficult to select among the many nucleophiles on the surface of the protein targeted for immobilization and it is difficult to distinguish between those nucleophiles on the protein and those in other biological molecules that may be present in a complex mixture. Thus, it is difficult to target a specific site in a specific protein for covalent attachment.

As such, there exists a need for structures and methods for covalent immobilization of proteins that does not rely upon nucleophilic moieties found in the side chains of naturally occurring amino acids.

SUMMARY OF THE INVENTION

In accordance with the purpose(s) of this invention, as embodied and broadly described herein, this invention, in one aspect, relates to covalently immobilizing proteins to a substrate.

In one embodiment, the invention is directed to a method of covalently immobilizing a protein, comprising (a) posttranslationally modifying a cysteine residue of said protein through the addition of functional groups, and (b) immobilizing said protein by ligation of said functional groups to a substrate; wherein said protein comprises one or more of a soluble protein or a solubilized protein.

In another embodiment, the invention is directed to a method of covalently immobilizing a protein, comprising (a) alkylating the sulfhydryl moiety in a C-terminal CaaX motif of a protein through a catalysis selected from the group consisting of catalysis of a farnesyl analog with protein farnesyltransferase and catalysis of a geranylgeranyl analog with protein geranylgeranyltransferase, resulting in the addition of a functional group, and (b) immobilizing the derivatized protein of (a) to a substrate comprising one or more of an azide-derivatized surface, an alkyne-derivatized surface and a phosphine-derivatized surface; wherein said protein comprises one or more of a soluble protein and a solubilized protein.

In a further embodiment, the invention is directed to an isolated protein comprising a soluble protein having a non-native C-terminal CaaX motif in which the cysteine has been posttranslationally modified, resulting in the addition of a functional group and wherein said protein has been immobilized to a substrate by ligating the functional group to said substrate.

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

DETAILED DESCRIPTION OF THE INVENTION

Figure 1:
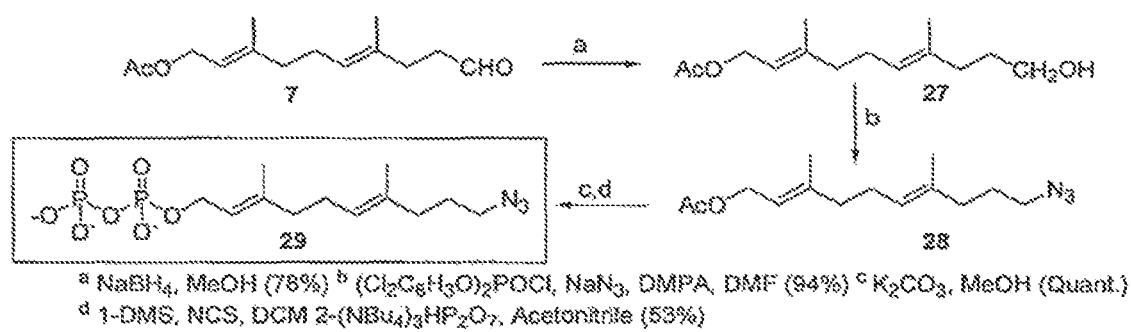
FIG. 1 depicts the synthesis scheme for farnesyl analog 10 AZDPP according to an embodiment of the invention.

The invention may be understood more readily by reference to the following detailed description of particular embodiments of the invention.

Particular advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Before the compositions and/or methods are disclosed and described, it is to be understood that this invention is not limited to specific compositions or methods, as such may, of course, vary, unless it is otherwise indicated. It is also to be understood that the terminology used herein is for the purpose of describing particular embodiments only and is not intended to be limiting.

DEFINITIONS

For the purposes of the invention, the following terms shall have the following meanings:

Moreover, for the purposes of the invention, the term "a" or "an" entity refers to one or more of that entity; for example, "a protein" refers to one or more of those elements or at least one element. As such, the terms "a" or "an", "one or more" and "at least one" can be used interchangeably herein. It is also to be noted that the terms "comprising," "including," and "having" can be used interchangeably. Furthermore, an element or means "selected from the group consisting of" or "comprising one or more of" refers to one or more of the elements in the list that follows, including mixtures (i.e. combinations) of two or more of the elements.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Reference will now be made in detail to particular embodiments of the invention.

In a certain embodiment, the invention relates to posttranslationally modifying a cysteine residue of a soluble or solubilized protein through the addition of functional groups, and immobilizing the protein by ligation of the functional groups to a substrate. In one embodiment, the cysteine is in a C-terminal CaaX motif of a soluble or solubilized protein and the posttranslational modification includes alkylation of the sulfhydryl moiety by a farnesyl analog through catalysis with a protein farnesyltransferase (PFTase) or alkylation by an analog through catalysis with a protein geranylgeranyltransferase (PGGTase), resulting in a modified cysteine residue in the protein. In another embodiment, the X of the CaaX motif is A, S, M, L or Q. In another embodiment, the C-terminal CaaX motif is not native to the protein In another embodiment, the functional group added through prenylation is an azide or an alkyne. In another embodiment, the substrate to which the protein is immobilized is a glass, a polymer, a gel or a metal surface. In a certain embodiment, a glass substrate is an azide-derivatized glass surface or a phosphine-derivatized glass surface.

In another embodiment, the invention relates to isolated proteins having a non-native C-terminal CaaX motif in which the cysteine has been posttranslationally modified, resulting in the addition of a functional group, wherein the protein has been immobilized to a substrate by ligating the functional group to the substrate.

In one embodiment of the invention, a method for the covalent immobilization of soluble proteins on a surface through an unnatural amino acid created by posttranslationally modifying a cysteine residue with functional groups, is described. In another embodiment the cysteine residue is posttranslationally modified with functional groups suitable for "click" chemistry or a Staudinger ligation. In another embodiment, protein farnesyltransferase (PFTase) or protein geranylgeranyltransferase (PGGTase) catalyzes the alkylation of the sulfhydryl moiety in the cysteine located in C-terminal CaaX motifs, by analogs of farnesyl diphosphate (FPP) or geranylgeranyl diphosphate (GGPP), as exemplified in FIG. 3. In a particular embodiment, the X of the CaaX motif is A, S, M, L or Q.

One embodiment of the invention includes farnesyl analogs. In another embodiment, farnesyl analogs have the general structure:

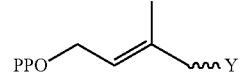

where Y represents the reactive group used to immobilize the modified protein.

Figure 9:
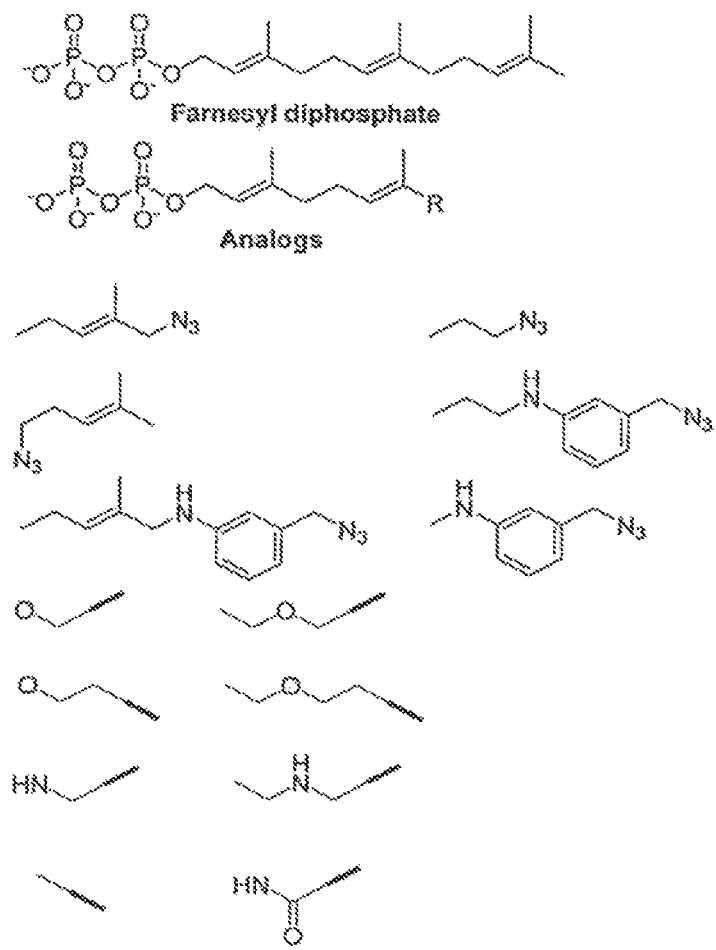
FIG. 9 depicts analogs of farnesyl diphosphate according to an embodiment of the invention.

In another embodiment, a farnesyl analog includes an analog comprising one or more of the analogs depicted in FIG. 9. Referring to FIG. 9 farnesyl diphosphate is shown for reference only and analogs are depicted as a base structure having an "R", with R group substituents shown thereafter.

In another embodiment, the surface to which a protein is immobilized includes silica, polymers, gels and metals. In another particular embodiment, a silicon surface includes silicon, glass slides, glass beads, $SiO_2$, and silicon nitride; a polymer surface includes polymer beads and polymer films; a gel includes agarose and acrylamide gels; and a metal includes surfaces, films, and particles of platinum, gold, silver, copper, zinc sulfide, cadmium selenide, zinc sulfide-capped cadmium selenide, titanium dioxide, aluminum and aluminum oxide, opal films, and ceramics. In one embodiment, a glass surface includes an azide-derivatized glass surface or a phosphine-derivatized glass surface.

In an embodiment of the invention, the method of immobilizing a protein is for the immobilization of a protein in a microdevice or "protein chip", a high-throughput screening device, for the microscopy of proteins on a surface, a sensor, a signaling device, a reactor for biocatalysis, or a tag for a bioassay.

In another embodiment of the invention, a protein to be immobilized includes a or solubilized protein. In another embodiment, a method of immobilizing a protein includes a method in which the native fold of the protein is preserved.

Particular proteins to be immobilized include but are not limited to enzymes, antibodies, hormones, antigenic proteins, receptor proteins, RNA and DNA binding proteins, signaling proteins, drug binding proteins, and pathogenic proteins. In another embodiment, proteins to be immobilized include but are not limited to hormone chorionic gonadotrophin receptor (HCG receptor), luteinizing hormone receptor, TEM-8 cell surface receptor, epidermal growth factor receptor, fibroblast growth factor receptor, insulin-like growth factor receptor, immunotoxins, and immunoconjugates.

The invention also includes isolated proteins having a non-native C-terminal CaaX motif in which the cysteine has been alkylated, resulting in the addition of a functional group where the protein has been immobilized to a surface by ligating the functional group to the surface.

EXAMPLES

It should be appreciated by those skilled in the art that the techniques disclosed in the examples which follow represent techniques discovered by the inventors to function well in the practice of the invention, and thus can be considered to constitute particular modes for its practice. However, those of skill in the art should appreciate, in light of the present disclosure, that many changes can be made in the specific embodiments disclosed herein which will still obtain a like or similar result without departing from the spirit and scope of the invention.

Example 1

Preparation of Modified Green Fluorescent Protein (GFP) with a PFTase Recognition Site The gene for the GFPuv protein was subcloned into a pQE-30Xa expression vector in order to append a $His_6$ sequence to the N-terminus and the C-terminal RTRCVIA PFTase recognition site. A 714 bp fragment from pGFPuv containing GFPuv was amplified by PCR. The forward primer contained 28 bases, 17 of which were complementary to the vector sequence upstream of the 5' end, FP-GFP: 5'-CCGGTAGCATGCATGAGTAAAGGAGAAG-3' (SEQ ID NO:1). The GFP start codon is indicated in bold, and a SphI site is underlined. The reverse primer contained 57 bases, 21 of which were complementary to the of the 3' end of RP-GFP: 5'-GACGATAAGCTTTTAAGCAATA-ACGCACCTAGTTCGTTTGTAGAGCTCATCCA TGCC-3' (SEQ ID NO:2). The primer contained a HindIII site (underlined), and a C-terminal yeast RTRCVIA farnesylation motif (bold). The PCR product was purified on a 1% agarose gel and extracted from the gel using the GFX™ PCR DNA Gel band purification kit, available from Amersham Biosciences. The purified DNA and pQE-30Xa, available from Qiagen were separately digested with SphI and HindIII and purified by GFX™ DNA purification kit, available from Amersham Biosciences, to obtain the 740 bp GFP-CVIA fragment and the 3477 bp linear pQE-30Xa vector, respectively. The two fragments were ligated using Quick T4 DNA ligase, available from New England Biolabs, and transformed into Epicurian coli XL1-Blue electrocompetent cells by electroporation. Cells were selected for growth on ampicillin/tetracyclin. Restriction analysis and sequencing confirmed the desired construct. Sequence analysis of pQE-GFP-CVIA indicated that the GFP-CVIA module was free of mutations. Ligation of the GFP-CVIA module into pQE-30Xa gave pQE-GFP-CVIA with GFP expression under control of the T5 promoter. The recombinant protein contained an N-terminal $His_6$ affinity tag and a C-terminal RTRCVIA PFTase recognition site.

Construct pQE-GFP-CVIA was transformed into chemically competent Epicurian coli M15(PREP4) cells, available from Qiagen. Starter cultures (10 mL of LB, 100 µg/mL ampicillin) were grown overnight at 37° C., with shaking. Three cultures, each containing 800 mL of LB (100 µg/mL ampicillin), were inoculated with 8 mL of the overnight culture and were grown at 37° C., with shaking at 240 rpm, until $OD_{600}$=0.6 when IPTG was added to 1 mM (final concentration), incubation was continued for 5 h, and cells were harvested by centrifugation and stored at −80° C. Cell paste (9 g) was resuspended in 36 mL sonication buffer (50 mM sodium phosphate, pH 8.0, 300 mM NaCl, 20 mM imidazole, 1 mM β-mercaptoethanol (BME), and 1 mM phenylmethanesulfonyl fluoride-PMSF). Cells were lysed by sonication, three periods of 30 s each. The sample was centrifuged for 30 min at 18000 rpm in a Beckman J20 rotor. The supernatant was mixed with 5 mL of Ni—NTA agarose resin, available from Qiagen) and shaken for 1 h at 4° C. GFP-CVIA was eluted from the resin with 250 mM imidazole. Fractions were screened by fluorescence and by SDS-PAGE. Pooled fractions were dialyzed against four changes of 50 mM Tris, pH=7.0, and 10 mM BME. Dialyzed enzyme was concentrated in a Centriprep centrifugal filter (10,000 cutoff, Millipore) and stored at −80° C. in 3:7 glycerol/water. A 1 L fermentation gave ~4.5 g of wet cell paste and ~10 mg of GFP-CVIA that was >95% pure by SDS-PAGE.

Example 2

Preparation of Modified Glutathione S-Transferase (GST) Protein a with PFTase Recognition Site The gene for the GST protein was subcloned into a pQE-30Xa in order to append an N-terminal $His_6$ affinity tag and a C-terminal RTRCVIA PFTase recognition site to the enzyme. A 660 bp fragment from pET-42b containing GST was amplified by PCR. The forward primer contained 33 bases, 21 of which were complementary to the vector sequence upstream of the 5'GST. FP_GST: 5'-ATACAT AAGCTTATGTCCCCTATACTAGGTTAT-3' (SEQID NO:3). The GST start codon is indicated in bold, and a BamHI site is underlined. The reverse primer contained 51 bases, 15 of which were complementary to the 3'end of GST RP-GST: 5'-TGAACCAAGCTTTTAGGCTA-TAACACAGCGCGTACGATCCGATTTTGGAGG-3' (SEQ ID NO:4). A HindIII site (underlined) and the C-terminal yeast farnesylation site (bold—encoding RTRCVIA) were introduced. The PCR product was purified on a 1% agarose gel and extracted using the GFX™ DNA purification kit. The purified DNA and pQE-30Xa, available from Qiagen, were separately digested with BamHI and HindIII and purified using a GFX™ DNA purification kit to obtain the 690 bp GST-CVIA fragment and the 3362 bp linear pQE-30Xa vector, respectively. The two fragments were ligated using Quick T4 DNA ligase, available from New England Biolabs, and transformed into XL1-Blue electrocompetent cells by electroporation. Cells were selected for growth on ampicillin/tetracyclin. Restriction analysis and sequencing confirmed the desired construct. Sequence analysis of pQE-GST-CVIA indicated that the GST-CVIA module was free of mutations. Ligation of the GST-CVIA module into pQE-30Xa yielded pQE-GST-CVIA with GST under control of the T5 promoter.

Construct pQE-GST-CVIA was transformed into chemically competent Epicurian coli M15(PREP4) cells, available from Qiagen. Starter cultures (10 mL of LB, 100 μg/mL ampicillin) were grown overnight at 37° C., with shaking. Three cultures, each containing 800 mL of LB (100 μg/mL ampicillin), were inoculated with 8 mL of the overnight culture and were grown at 37° C., with shaking at 240 rpm, until $OD_{600}$=0.6 when IPTG was added to 1 mM (final concentration), incubation was continued for 5 h, and cells were harvested by centrifugation and stored at −80° C. Cell paste (10 g) was resuspended in 50 mL of sonication buffer (50 mM sodium phosphate, pH 8.0, 300 mM NaCl, 20 mM imidazole, 1 mM β-mercaptoethanol (BME), and 1 mM phenylmethanesulfonyl fluoride (PMSF). Cells were lysed by sonication, three periods of 30 s each. The sample was centrifuged for 30 min at 18000 rpm in a Beckman J20 rotor. The supernatant was mixed with 5 mL of Ni—NTA agarose resin, available from Qiagen, and shaken for 1 h at 4° C. The resin was loaded onto a column. The flow through was collected and the column was eluted with washing buffer (sonication buffer minus PMSF) until the absorbance at 280 nm decreased to baseline. GST-CVIA was eluted with washing buffer containing 250 mM imidazole. Fractions were screened for GST activity using the GST.Tag Assay Kit, available from Novagen, and by SDS-PAGE. Pooled fractions were dialyzed four times against 15 mM Tris, pH 7.0, and 10 mM BME. Dialyzed enzyme was concentrated in a Centriprep centrifugal filter 10,000 cutoff, available from Millipore, and glycerol was added to 30%. The sample was flash frozen in liquid nitrogen and stored at −80° C. One liter of cell culture produced ~5 g of wet cell paste and ~12 mg of GST-CVIA that was at least 95% pure by SDS-PAGE.

Example 3

Preparation of Farnesyl Analogs

The general synthesis scheme for the preparation of compound 10-Azido-Disphosphate (10 AZDPP) is set forth in FIG. 1.

Figure 2:
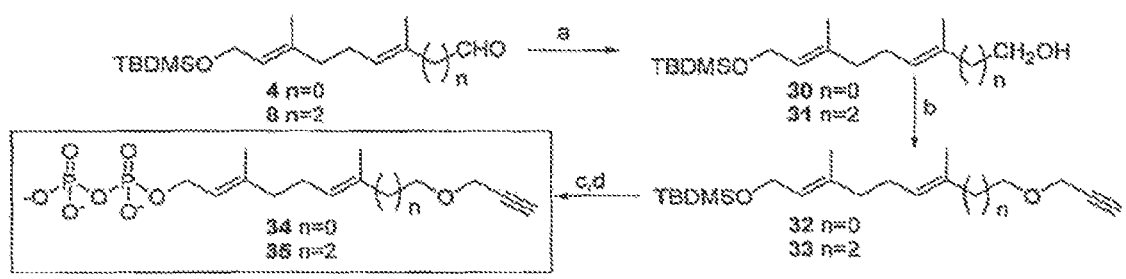
FIG. 2 depicts the synthesis scheme for propargyl ether derivatives of farnesyl diphosphate according to an embodiment of the invention.

The general synthesis scheme for the preparation of propargyl ether derivatives of farnesyl diphosphate is set forth in FIG. 2.

Figure 10:
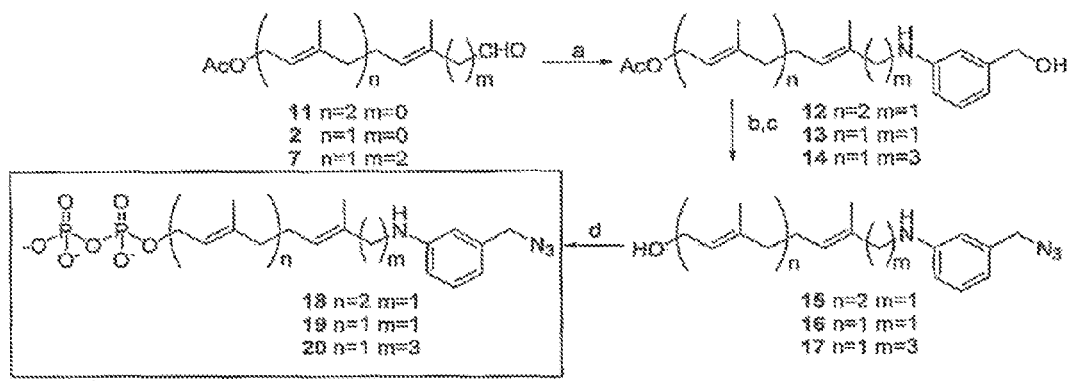
FIG. 10 depicts the synthesis scheme for benzylazide derivatives of farnesyl diphosphate according to an embodiment of the invention.

The general synthesis scheme for the preparation of benzylazide derivatives of farnesyl diphosphate is set forth in FIG. 10.

Figure 11:
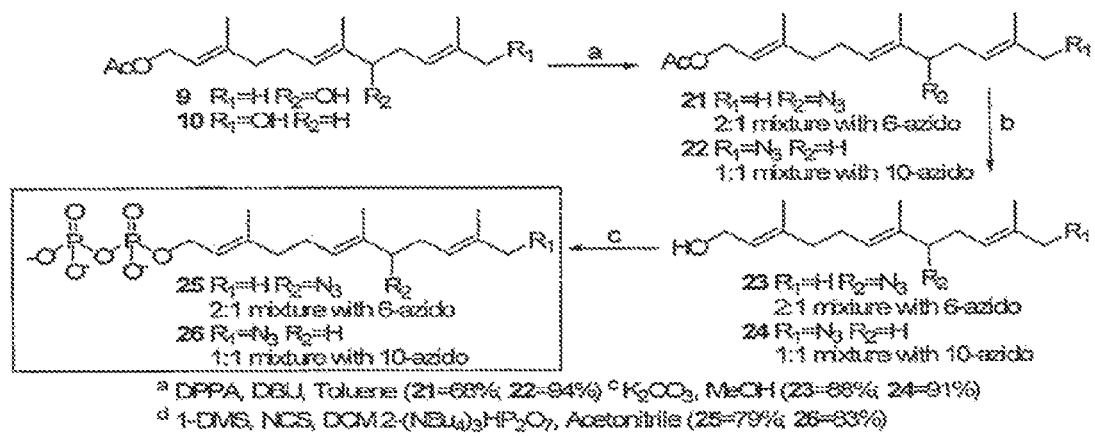
FIG. 11 depicts the synthesis scheme for prenyl azide derivatives of farnesyl diphosphate according to an embodiment of the invention.

The general synthesis scheme for the preparation of prenyl azide derivatives of farnesyl diphosphate is set forth in FIG. 11.

Figure 12:
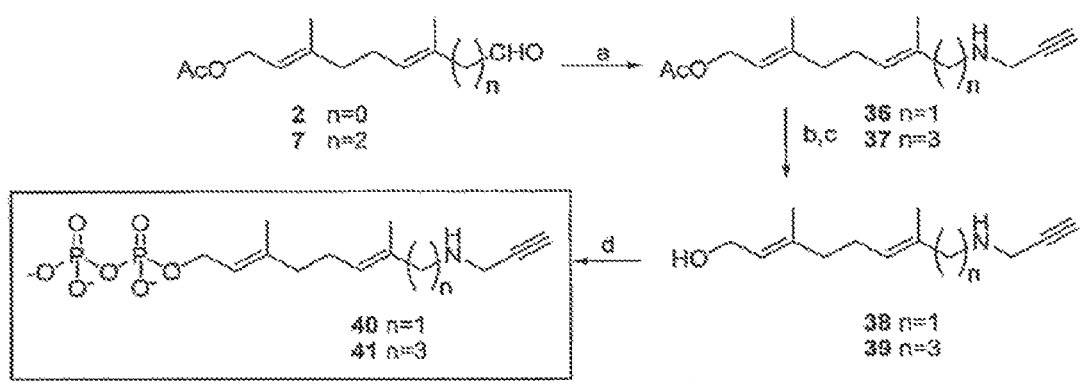
FIG. 12 depicts the synthesis scheme for propargylamine ether derivatives of farnesyl diphosphate according to an embodiment of the invention.

The general synthesis scheme for the preparation of propargylamine derivatives of farnesyl diphosphate is set forth in FIG. 12.

Figure 13:
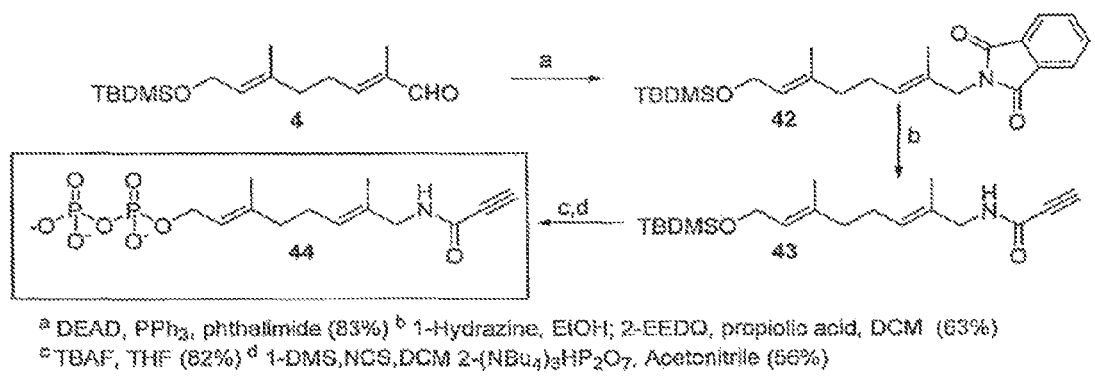
FIG. 13 depicts the synthesis scheme for propalamide ether derivatives of farnesyl diphosphate according to an embodiment of the invention.

The general synthesis scheme for the preparation of propalamide derivatives of farnesyl diphosphate is set forth in FIG. 13.

Example 4

In Vitro Farnesylation of GFP-CVIA and GST-CVIA

Figure 3:
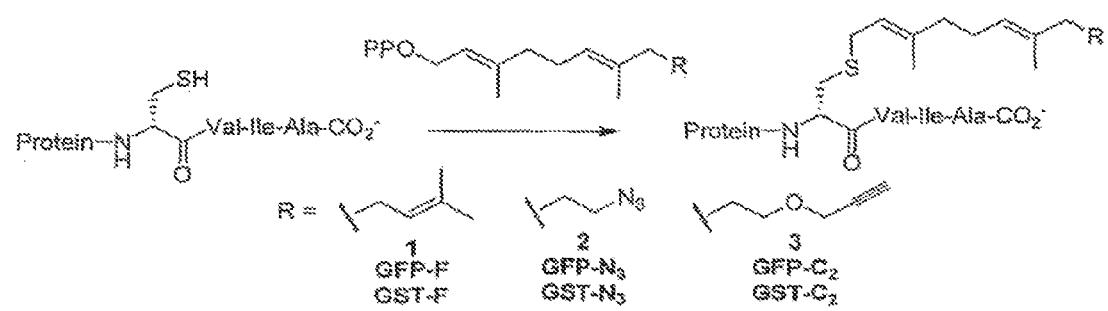
FIG. 3 depicts the modification scheme for Green Fluorescent Protein (GFP) and Glutathione S-transferase (GST) with CaaX recognition motifs inserted according to an embodiment of the invention.

Purified GFP-CVIA or GST-CVIA (20 μl; 350 μM) and 1.8 mM of farnesyl diphosphate or an analog prepared as described herein (4 μL) were added to 156 μL of 25 mM phosphate buffer, pH 7.0, containing 10 mM $MgCl_2$, and 10 μM $ZnSO_4$. The sample was incubated at 30° C. for 10 min before addition 10 μL of yeast PFTase (250 nM), obtained from pET42-RAM2/RAM1 using the method of Harris et al. Biochemistry 2002, 41, 10554-10562. After 1 hour at 30° C. an additional 20 μL of GFP-CVIA or GST-CVIA and 10 μL of PFTase were added and the incubation was continued for 1 h. The samples were concentrated using Centricon YM-10, available from Millipore, and the concentration of total protein was determined by Bradford analysis. A generalized reaction scheme is shown in FIG. 3. Farnesylation of GFP-CVIA with 10 AZDPP and PE10DPP result in products referred to as GFP-$N_3$ and GFP-$C_2$, respectively. Farnesylation of GST-CVIA with 10 AZDPP and PE10DPP result in products referred to as GST-$N_3$ and GST-$C_2$, respectively. Farnesylation of GFP-CVIA and GST-CVIA with farnesyl diphosphate result in products referred to as GFP-F and GST-F, respectively.

Example 5

Immobilization of Derivatized Proteins

A. Immobilization by "Click" Ligation

Figure 4:
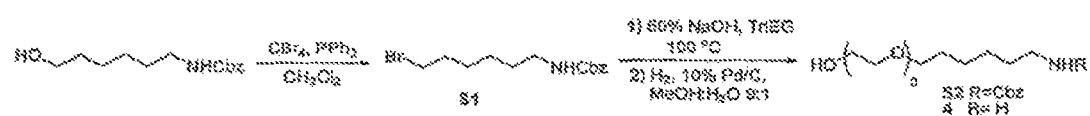
FIG. 4 depicts the synthesis scheme for linker 4 according to an embodiment of the invention.
Figure 5:
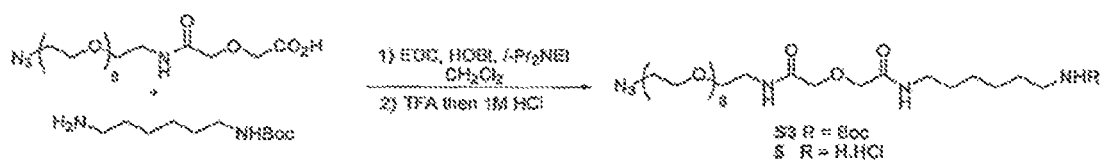
FIG. 5 depicts the synthesis scheme for linker 5 according to an embodiment of the invention.

Amine-coated glass slides were treated with a solution of N,N'-disuccinimidyl carbonate (DSC, 15 mM) and N,N-diisopropylethylamine (DIPEA, 15 mM) in DMF overnight at rt with shaking. The slides were washed five times (5 min each) with DMF and dried under $N_2$. The succinimidyl derivatized slides were treated with a 5:1 solution of linker 4 and linker 5, the synthesis of which are set out in FIGS. 4 and 5 respectively, (5 mM total concentration) and DIPEA (5 mM) in DMF overnight at rt. The slides were rinsed with EtOAc (5 times-5 min each), dried under $N_2$ and then capped by treatment with a solution of ethanolamine (50 mM) in DMF for 3 h at rt. The blocked slides were rinsed with EtOAc (5 times-5 min each) and dried under $N_2$.

One microliter of a solution of alkyne-derivatized proteins GFP-$C_2$ and GST-$C_2$ and $Cu^+$ complex (1.7 mM final concentration, prepared by mixing equal volumes of tris-benzyltriazolylmethylamine (TBTA),[2] $CuSO_4$ and TCPE (20 mM each)), in 1:3 glycerol/water was spotted into wells on azido slides masked with a silicon membrane. The slides were kept in a humid chamber at 4° C. for 3 h before Block It™ solution (4 μL) was added to each well and then were returned to the chamber for 5 h. The slides were washed with PBST (5 min each), appropriate fluorescently-tagged antibodies (4 μg/mL) were added to the wells (4 μL), and the plates were incubated at 4° C. The slides were then washed with PBST (5 times-5 min each) and scanned using a Typhoon 8600 Variable Mode Imager.

The concentrations of spotted GFP-$C_2$ and GST-$C_2$ varied from 1 to 20 μM. No fluorescent signal was seen when the antibodies were added to control wells that did not contain GFP or GST proteins. In order to distinguish between specific and non-specific binding, GFP-F and GST-F bearing a farnesyl group instead of the reactive alkyne moiety were used as controls. Background fluorescence was seen for both of the farnesylated proteins. The fluorescence signals for wells containing proteins with covalently attached alkyne groups were easily detected and significantly above background. Over a range of 1-10 μM, the intensity of the signal increased by ~50% for each 2-fold increase in the concentration of the derivatized protein.

The antibodies could be removed by treatment with an acidic saline solution (125 mM glycine, 500 mM NaCl, 2.5% Tween 20®, pH 2) for 2 h at 80° C. Incubation of the stripped slides with anti-GFP for 16 h at 4° C., only gave signals corresponding to locations of immobilized GFP. A second cycle of stripping, followed by incubation with anti-GST only gave signals at the locations of immobilized GST. Thus, GFP and GST remain attached to the slides under conditions sufficiently stringent to disrupt interactions between the immobilized proteins and their respective antibodies.

In another experiment, GFP-$C_2$ (25-100 µM) was immobilized by the "click" procedure set forth above, and the slide was analyzed directly by phosphorimaging without conjugation with fluorescent antiGFP. A fluorescent signal was detected after the slide had been thoroughly washed with PBST. The slide was then allowed to stand in phosphate buffer (pH 7.0) at 4° C. for two days. After two days, the signal had only diminished by 22%. Thus, GFP retained its native fold during the immobilization and subsequent storage in buffer.

B. Immobilization by Staudinger Ligation

Diphenylphosphinothiol was attached to amine-derivatized slides according to the procedure set forth by Soellner et al. *J. Am. Chem. Soc.* 2003, 125, 11790-11791 to give a surface-bound phosphinothioester.

Azido-derivatized proteins GFP-$N_3$ and GST-$N_3$ in DMF/$H_2O$ (50:1) were added to phosphinothioester slides by spotting 1 µL with into the appropriate well. The Staudinger ligation was allowed to proceed for 1.5 h in an enclosed chamber saturated with DMF. Block It™ solution (4 µL) was added to each well and the slides were allowed to stand for 2.5 h. The slides were washed once with DMF and four times with PBST (5 min each). Four microliters of a solution of the appropriate antibodies (4 µg/mL) were added to the wells and the plates were incubated at 4° C. The slide was then washed with PBST (5 times-5 min each) and scanned with a Typhoon 8600 Variable Mode Imager.

Visualization of GFP-$N_3$ and GST-$N_3$ by fluorescent antibodies yielded a detectable signal, indicating that the proteins were successfully immobilized, but control slides with GFP-F and GST-F had high backgrounds. Lower backgrounds were achieved when the ligation was carried out in 50:1 DMF/water.

In a separate experiment, GFP-$N_3$ was immobilized by the Staudinger ligation as set forth above and the slides were stored in buffer and visualized by direct imaging of the GFP fluorophore over a period of 6 days. The fluorescence intensity of spots corresponding to immobilized GFP-$N_3$ and the GFP-F control decreased during the first 4 days; however, the difference between the intensities for immobilized GFP and the control remained constant. After 4 days signals for the control samples were reduced to background levels; whereas, the signal for covalently bound GFP remained constant, indicating a stable immobilization of the protein on the substrate.

Example 6

Immobilization of Proteins on a Gold Particle Substrate

Linker protected gold nanoparticles were generally produced as follows. Acetic acid (12.5% of the total final volume) was dissolved in MeOH (87.5% final total volume) in a Teflon vial. Linkers (75 mM total final volume concentration), produced as described herein, were added to the acetic acid MeOH solution and allowed to shake for 5 min. Hydrogen tetrachloroaurate(III) trihydrate (gold source, 75 mM final concentration) was added to the linker solution and allowed to shake for 10 min. Then $NaBH_4$ (750 mM) was added and the reaction was allowed to stir overnight. The linker protected gold nanoparticles were purified using a 10K MW cutoff Slide-A-Lyzer® Dialysis Cassette and dialyzed in a 1:1 (v:v) mixture of HPLC grade MeOH and nanopure water. Dialysis solution was changed three times. Purified particles were transferred to a clean Teflon vial and MeOH was concentrated on rotoevaporator and the water was removed by lypothozation.

A. General Procedures for Click Chemistry Assay

Gold nanoparticles were re-suspended in MeOH to an approximate concentration of 0.75 mM reactive linker. Fluorescent probe dissolved in tert-butyl alcohol was added to 100 µL of nanoparticles stock for final concentration of 213 nM and 219 nM respectively. $CuSO_4$ was dissolved in tert-butyl alcohol:water (1:1, v:v) followed by the addition of TBTA and sodium ascorbate to give a final concentration of 358 nM, 384 nM and 9 mM, respectively. This freshly prepared solution was added to the reaction mixture and allowed to shake for ten days. Products were purified using a 10K MW cutoff Slide-A-Lyzer® Dialysis Cassette and dialyzed in a 1:1 (v:v) mixture of HPLC grade MeOH and nanopure water. Dialysis solution was changed three times. Purified particles were transferred to a clean Teflon vial and MeOH was concentrated on rotoevaporator and the water was removed by lypothozation.

B. Preparation of Azide and Hydroxyl Protected Gold Nanoparticles

Figure 6:
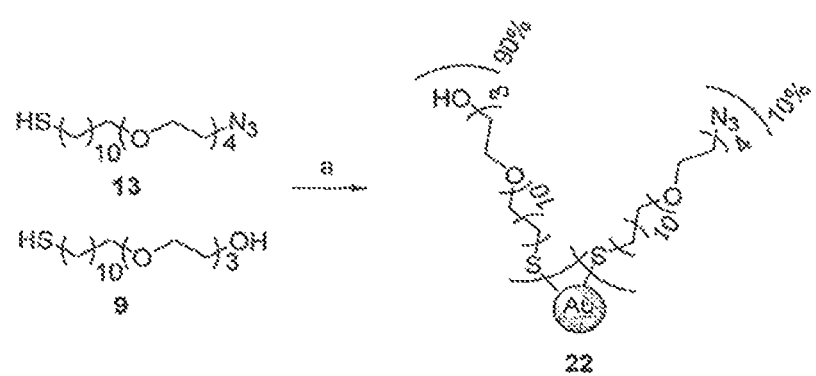
FIG. 6 depicts the synthesis scheme for the production of Azide and hydroxyl protected gold nanoparticles according to an embodiment of the invention.

Azide and hydroxyl protected gold nanoparticles were produced using the scheme generally set forth in FIG. 6. Thiols 13 and 9 were added to solution a (HOAc (12.5% total volume) dissolved in MeOH for a final reaction concentration of 0.75 mM and 6.75 mM, respectively. $HAuCl_4.3H_2O$ was added to give a final concentration of 75 mM. $NaBH_4$ was dissolved in MeOH immediately before addition to the reaction vial). The resulting particles (22) were deposited onto 200 mesh, CU silicon Monoxide support film (Ted Pella, Inc.).

C. Preparation of Alkyne and Hydroxyl Protected Gold Nanoparticles

Figure 7:
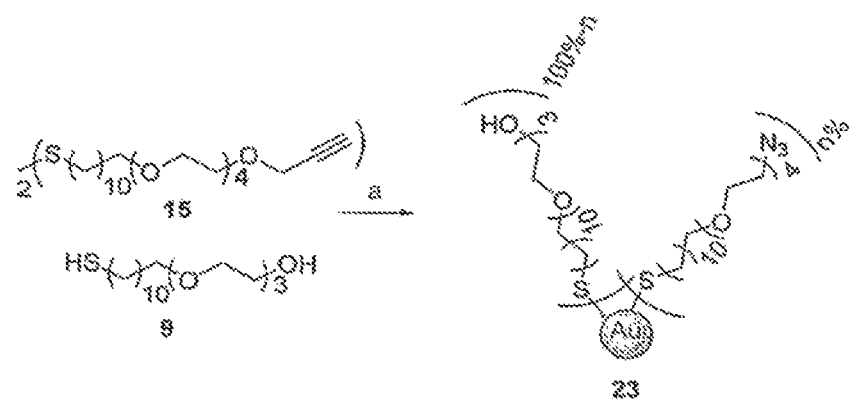
FIG. 7 depicts the synthesis scheme for the production of Alkyne and hydroxyl protected gold nanoparticles according to an embodiment of the invention.

Alkyne and hydroxyl protected gold nanoparticles were produced using the scheme generally set forth in FIG. 7. Thiols 13 and 9 were added to solution a (HOAc (12.5% total volume) dissolved in MeOH for a final reaction concentration of 0.38 mM and 6.75 mM, respectively. $HAuCl_4.3H_2O$ was added to give a final concentration of 75 mM. $NaBH_4$ was dissolved in MeOH immediately before addition to the reaction vial). The resulting particles 23 were deposited onto 200 mesh, CU silicon monoxide support film.

D. Preparation of Azide Protected Gold Nanoparticles Coupled to Dansyl-Alkyne

Figure 8:
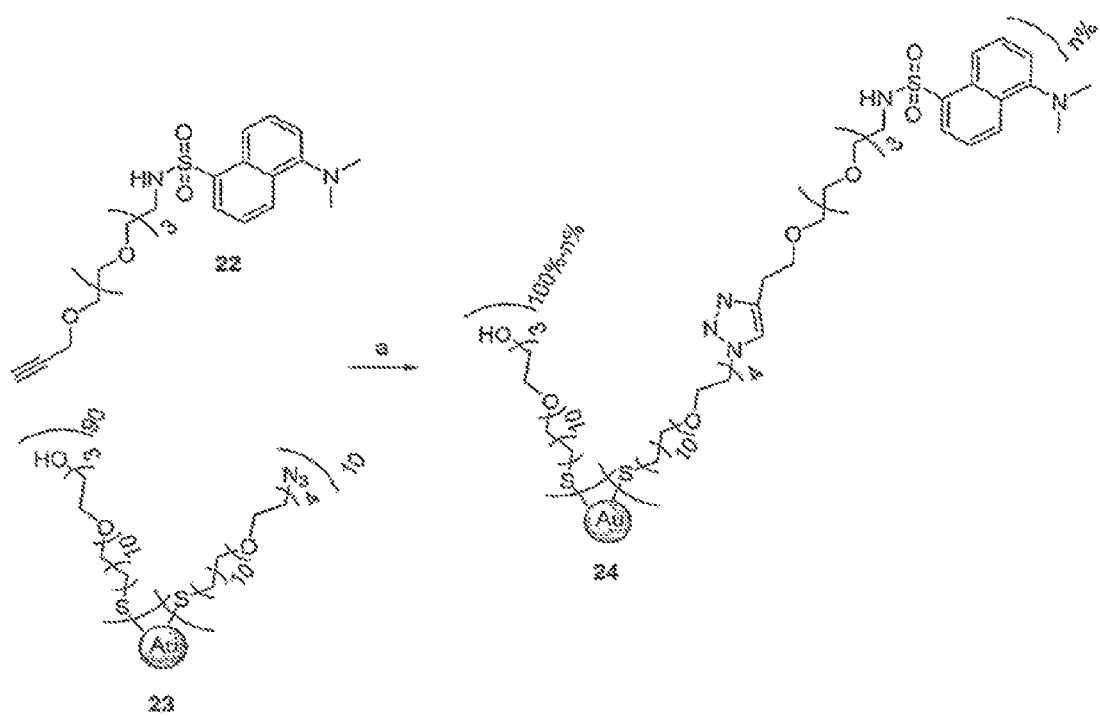
FIG. 8 depicts the synthesis scheme for the production of Azide protected gold nanoparticles coupled to dansyl-alkyne according to an embodiment of the invention.

Azide protected gold nanoparticles were coupled to dansyl-alkyne using the scheme generally set forth in FIG. 8 in a reaction containing $CuSO_4$, TBTA, and Sodium ascorbate, at room temperature, overnight.

The compositions and methods disclosed and claimed herein can be made and executed without undue experimentation in light of the present disclosure. While the compositions and methods of this invention have been described in terms of particular embodiments, it will be apparent to those of skill in the art that variations may be applied to the compositions and methods and/or in the steps or in the sequence of steps of the methods described herein without departing from the concept, spirit and scope of the invention. More specifically, it will be apparent that certain related components may be substituted for the components described herein while the same or similar results would be achieved. All such similar substitutes and modifications apparent to those skilled in the art are deemed to be within the spirit, scope and concept of the invention as defined by the appended claims.

What is claimed is:

1. A method of covalently immobilizing a protein, comprising:
   a. posttranslationally modifying a cysteine residue of said protein through the addition of functional groups, and
   b. immobilizing said protein by ligation of said functional groups to a substrate;
   wherein said protein comprises a soluble protein or a solubilized protein, and wherein said substrate comprises one or more of an azide-derivatized surface and an alkyne-derivatized surface.

2. The method of claim 1, wherein said cysteine is in a C-terminal CaaX motif of a soluble protein.

3. The method of claim 2, where X is A, S, M, L or Q.

4. The method of claim 1, wherein said posttranslational modification of a cysteine includes alkylation of the sulthydryl moiety comprising one or more of catalysis of a farnesyl analog with protein farnesyltransferase and catalysis of a geranylgeranyl analog with protein geranylgeranyltransferase.

5. The method of claim 4, where said functional group comprises one or more of an azide, an alkyne, an alkene, a ketone and an alkoxyamine.

6. The method of claim 4, wherein said farnesyl analog is selected from the analogs depicted in FIG. 9.

7. The method of claim 1, wherein said functional group comprises one or more of an azide and an alkyne.

8. The method of claim 1, wherein said substrate comprises one or more of a silicon surface selected from the group consisting of silicon, glass, $SiO_2$, and silicon nitride, a polymer surface comprising one or more of polymer beads and polymer films, a gel surface comprising one or more of an agarose gel and an acrylamide gel, and a metal surface comprising one or more of platinum, gold, silver, copper, zinc sulfide, cadmium selenide, zinc sulfide-capped cadmium selenide, titanium dioxide, aluminum, aluminum oxide, opal films, and ceramics.

9. The method of claim 8, wherein said substrate comprises one or more of an azide-derivatized glass surface and an alkyne-derivatized glass surface.

10. A method of covalently immobilizing a protein, comprising:
   a. alkylating the sulthydryl moiety in a C-terminal CaaX motif of a protein through a catalysis selected from the group consisting of catalysis of a farnesyl analog with protein farnesyltransferase and catalysis of a geranylgeranyl analog with protein geranylgeranyltransferase, resulting in the addition of a functional group, and b. immobilizing the derivatized protein of (a) to a substrate comprising one or more of an azide-derivatized surface and an alkyne-derivatized surface;

wherein said protein comprises one or more of a soluble protein and a solubilized protein.

11. The method of claim 10, where X is A, S, M, L or Q.

12. The method of claim 10, where said functional group comprises one or more of an azide, an alkene, an alkyne, a ketone, or an alkoxyamine.

13. The method of claim 10, wherein said farnesyl analog is selected from the analogs depicted in FIG. 9.

* * * * *